United States Patent [19]
Hoefer et al.

[11] 3,994,189
[45] Nov. 30, 1976

[54] ELECTROPHORESIS GEL SLICER APPARATUS AND METHOD

[75] Inventors: Stanton A. Hoefer; John C. DiFonzo, both of San Francisco, Calif.

[73] Assignee: Hoefer Scientific Instruments, San Francisco, Calif.

[22] Filed: July 16, 1975

[21] Appl. No.: 596,318

[52] U.S. Cl. .................................. 83/56; 83/459; 83/751
[51] Int. Cl.[2] ...................... B26D 1/10; B26D 3/16; B26D 4/06
[58] Field of Search ............. 83/751, 752, 759, 458, 83/459, 56

[56] References Cited
UNITED STATES PATENTS
775,247  11/1904  Reid...................... 83/759

FOREIGN PATENTS OR APPLICATIONS
1,502,864  1/1970  Germany ............................ 83/751
40,029  10/1972  Japan.................................. 83/751

*Primary Examiner*—Willie G. Abercrombie

[57] ABSTRACT

A slicer for tube gels or strips from a slab gel which includes a cutting plate having a plurality of blades in spaced parallel relation extending between the sides of the cutting plate. The spaces between the blades are configured with a cutting edge on one side thereof. The plate is mounted in a holder which is driven by a rotating cam mounted on a drive motor shaft which contacts a cam follower on an arm attached to the cutting plate holder. A pedestal is provided for supporting the gel slab strip or tube gel. The gel is retained laterally on the pedestal by means of retaining vanes on each side of the pedestal. The retaining vanes are urged by springs to extend above the surface of the pedestal. The cutting plate holder is rotatably attached to a framework for mounting the drive motor and the support pedestal so that it may be alternately positioned overlying the pedestal and in a remote position. A weight is attached to the cutting plate holder which is radially adjustable about the axis of rotation of the cutting plate holder. Adjustment of the radius of the weight from the axis of rotation allows adjustment of the force applied to the cutting plate holder for urging the cutting plate toward the pedestal. A gel to be sliced is placed on the pedestal, the cutting plate is positioned to overlie the gel with the cutting edges of the plurality of blades in contact with the gel, and the motor is actuated causing reciprocating motion of the cutting blades. The cutting blades advance through the gel depressing the springs supporting the retaining vanes, thereby pushing the retaining vanes ahead of the cutting blades until the cutting blades pass through the gel and contact the surface of the pedestal.

11 Claims, 7 Drawing Figures

ELECTROPHORESIS GEL SLICER APPARATUS AND METHOD

BACKGROUND OF THE INVENTION

This invention relates to a gel slicer for use in slicing strips from a slab gel or tube gels, and more particularly to such a gel slicer for cutting a plurality of uniform gel slices simultaneously.

Polyacrylamide gels are sliced after electrophoresis for the purpose of anaylzing the activity of the molecules resolved by the gel system and for determination of the pH in the gel. The activity of the molecules may refer to enzyme activity, biological activity, immunological activity, or radioactivity. Enzyme activity is measured by an enzyme assay of the slice containing the enzyme. Biological activity may be measured in various ways including the stimulation or inhibition of the growth of cells by the contents of a slice. Immunological activity may be determined by radioimmunological assay of the contents of a slice, by immuno-diffusion or immuno-electrophoresis. Radioactivity in a slice is determined by scintillation count or autoradiography of the slice. pH measurement is done on a deaerated distilled water extract of a slice and is used to determine the moving boundary in the gel or the determination of the pH gradient in an isoelectric focused gel.

Prior art gel slicing apparatus included a type utilizing a razor blade operating in a guilliotine type device for cutting single slices from a gel separately. Another type of gel slicer utilizes a continuous wire which is laid down laterally across a slot and around pins at the sides of the slot, thereby providing a series of transverse parallel lengths of wire. The gel holder in this latter device consists of a trough with slots extending perpendicular to the trough length and having a depth extending through the bottom of the trough. The gel is placed in the trough and the wire array is forced down on the top of the gel with the wires entering the laterally extending slots. Often times the wires contact the edges of the slots and break, or the tension in the wire changes eliminating any possibility for uniform slice thickness or a clean cut through the gel. Electric gel slicers are available in which the gel is frozen to an advancing stage and a single blade cuts off segments separately at preset thickness. These methods all have disadvantages relative to providing uniform slices from the gel and nearly always impart distortion to the gel during the cutting process.

A device is needed for providing simultaneous slicing of uniform slices along the entire length of a particular gel.

SUMMARY AND OBJECTS OF THE INVENTION

The disclosed gel slicer includes a framework and a means for firmly holding the gel mounted on the framework for positioning overlying the means for holding the gel. A slicing grid has a plurality of blade members in spaced parallel relation with cutting edges disposed toward the means for holding the gel defining a cutting axis direction. Means is provided for driving the slicing grid in reciprocating motion in the direction of the cutting axis of the blade members. Further means is provided for urging the slicing grid toward the means for holding the gel so that when a gel is placed on the means for holding and the slicing grid is positioned overlying the gel, the means for driving the slicing grid is actuated and the gel is simultaneously separated into a plurality of slices.

In general it is an object of the present invention to provide a gel slicer which will simultaneously slice a complete gel into slices of uniform thickness.

Another object of the invention is to provide a gel slicer which is capable of cleanly slicing gels of any concentration.

Another object of the invention is to provide a gel slicer which slices the gel at room ambient temperature and prevents distortion in the gel during slicing.

Additional objects and features of the invention will appear from the following description in which the preferred embodiment has been set forth in detail in conjunction with the accompanying drawings.

DESCRIPTION OF THE PREFERRED EMBODIMENT

Figure 1:
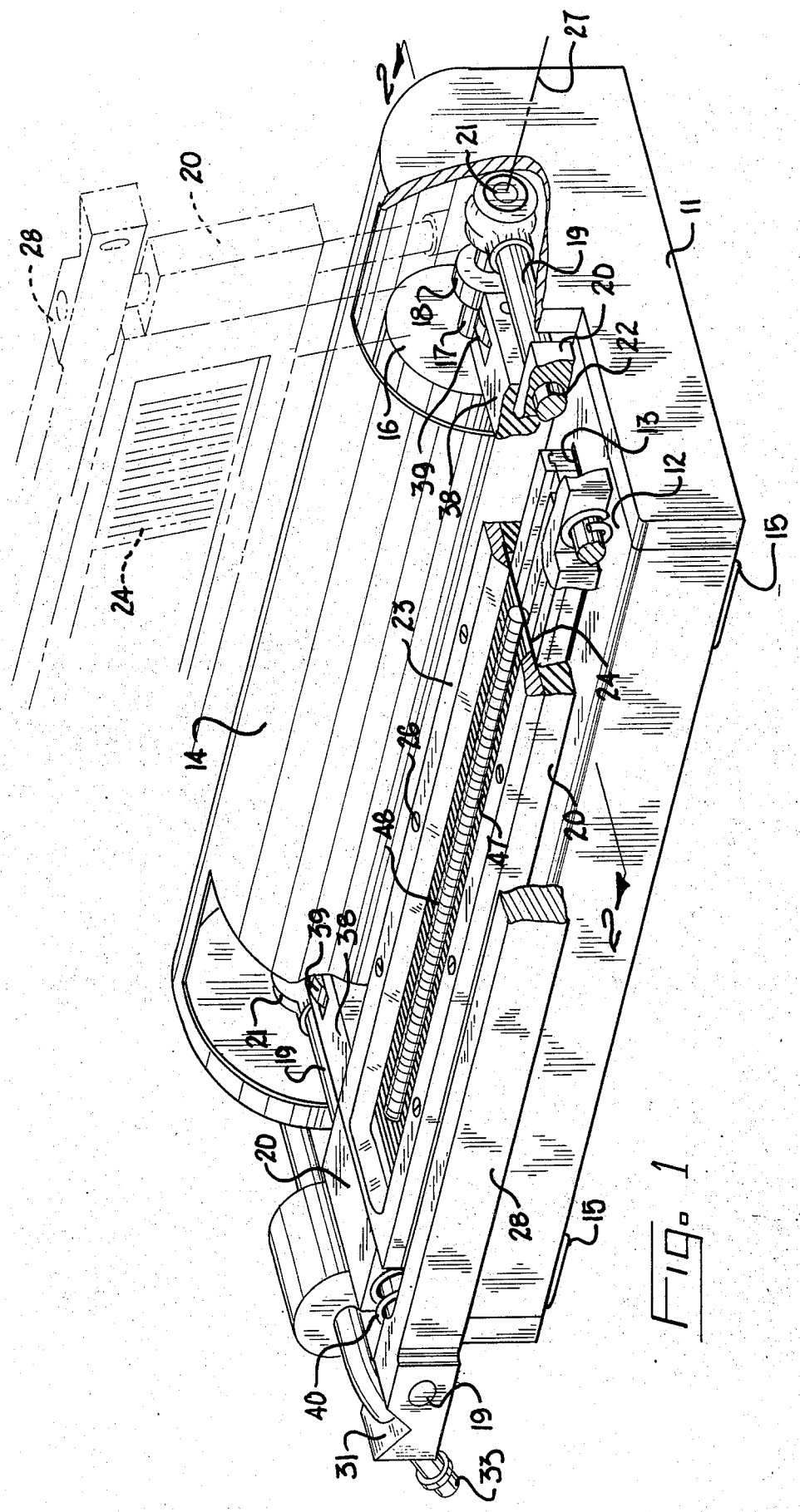
FIG. 1 is an isometric view of the disclosed gel slicer.

Referring to FIG. 1 a framework 11 is shown having a front portion 12 with a well 13 located therein, and having a rear portion 14 for containing a motor 16. Feet 15 are provided for supporting framework 11. An output shaft 17 is driven rotationally by motor 16. A cam 18 is mounted on shaft 17. An arm 19 is mounted on either end of shaft 17 in this embodiment, connected thereto by means of rod end bearings 21. A cutting grid holder 20 has a through bore 22 on each end formed to pass one of the arms 19, thereby providing for sliding movement between arms 19 and cutting grid holder 20. A cutting grid or plate 24 is mounted on cutting grid holder 20 and is retained thereon by an upper retaining plate 23. Retaining plate 23 is secured in a position overlying cutting plate 24 by some fastening means such as screws 26. Cutting grid holder 20 is rotatable on arms 19 about an axis 27 through rod end bearings 21. Cutting plate 24 may therefore be positioned overlying well 13 or remotely in an upper out of the way position shown in ghost line in FIG. 1.

Figure 5:
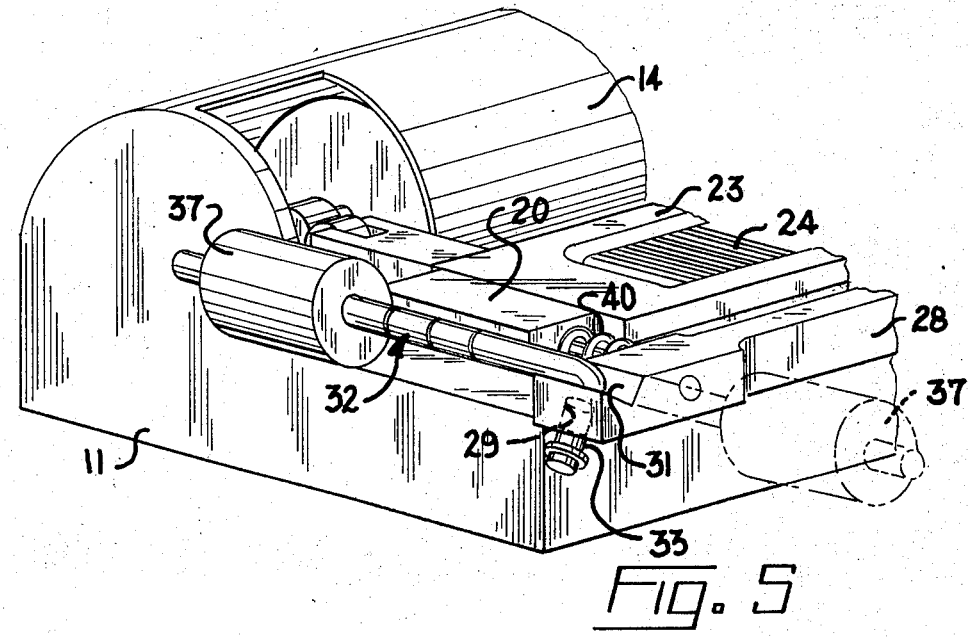
FIG. 5 is a partial isometric view showing the means for urging the cutting plate toward a gel to be sliced.

Arm 19 extending through bores 22 in cutting plate holder 20 have mounted between the ends thereof a transverse member 28. Referring to FIG. 5, a hole 29 is seen passing through each end of transverse member 28. A groove 31 is formed laterally at each end of transverse member 28 in communication with hole 29, and an L shaped rod 32 has a first portion 33 passing through hole 29 and a second portion 34 lying in groove 31. First portion 33 of rod 32 has a ring 36 in the end thereof to retain rod 32 in hole 29. A weight 37 is slidably attached to the second portion 34 of rod 32. Rod 32 is configured so that portion 34 may be lifted out of groove 31 and rotated through 180° to take up a position as seen in ghost line in FIG. 5.

A cam follower arm 38 is attached to either end of cutting plate holder 26. A cam follower 39 is attached to the end of each of cam follower arms 38 for contact with can 18. Compression springs 40 surround arms 19 between transverse member 28 and cutting plate holder 20 to force cam followers 39 into continuous contact with cams 18.

Figure 6:
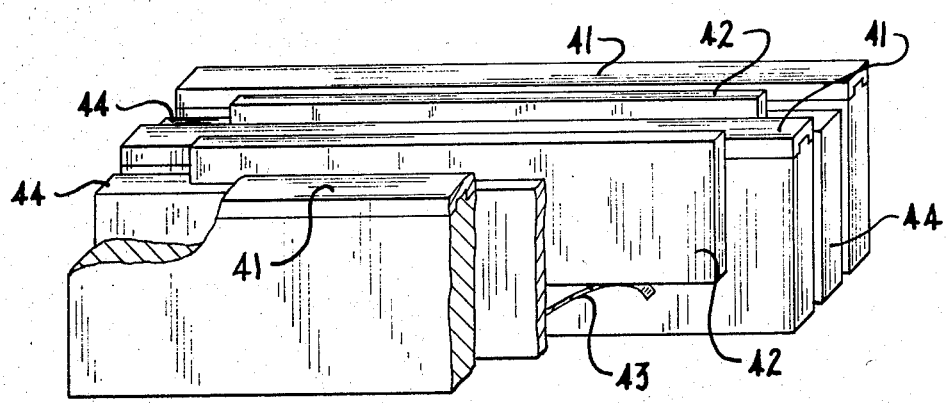
FIG. 6 is a partial isometric view showing the gel support pedestal assembly.

A gel support pedestal and a gel retaining assembly are formed to fit in well 13. FIG. 6 shows a detailed view of an assembly for insertion in well 13 including a plurality of gel support pedestals 41 together with first and second retaining vanes 42. Retaining vanes 42 are placed on either side of one or more gel support pedestals 41 for retaining or stopping a gel strip from a gel slab or a gel tube laterally thereon. A leaf spring 43 urges each of retaining vanes 42 upward as seen in FIG. 6, so that the top edge of retaining vanes 42 is initially above the surface of gel support pedestal 41. A vane retention plate 44 is attached to gel support pedestal 41 on either side thereof so that gel retaining vanes 42 may translate upward and downward as seen in FIG. 6 without moving laterally relative to gel support pedestals 41.

Figure 7:
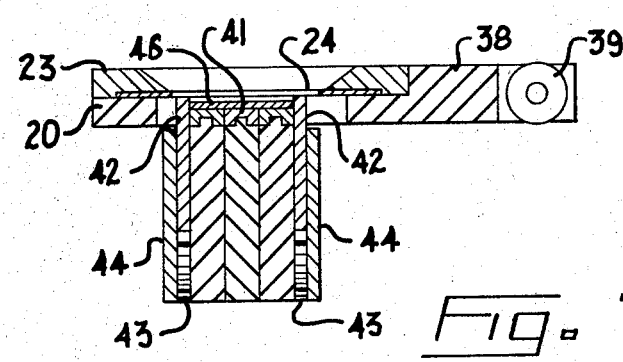
FIG. 7 is a sectional view showing a gel support pedestal configuration for wider gels.

Turning now to FIG. 7, a sectional drawing of the gel support pedestal and gel retention vane assembly is undertaken. A strip 46 from a gel slab is shown mounted on top of support pedestals 41 which lie adjacent to one another to provide a wide gel support pedestal 41.

Figure 4:
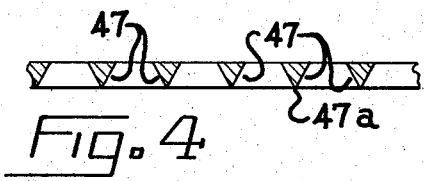
FIG. 4 is a partial sectional view along the line 4—4 of FIG. 3.
Figure 3:
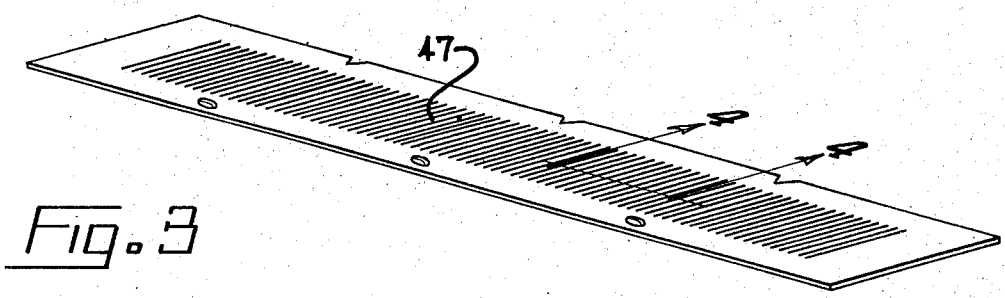
FIG. 3 is an isometric view of the cutting plate in the disclosed invention.

FIG. 3 shows a cutting plate 24 which is fabricated from a stainless steel plate in this embodiment. Cutting blades 47 may be formed by a photoetch process which is well known in the art. In brief review, the thin stainless steel plate is coated with photoresist, exposed through a mask, the resist removed in those areas where etching is desired, and the plate dipped in an etching solution with the stabilized photoresist remaining on the surface of the plate where no etching is desired. Such a process provides the cutting blades 47 seen in sectional view in FIG. 4. The angle on the cutting edge of the blades 47 is about 60°. Moreover, the cutting edge 47A on blades 47 is slightly serrated due to the slight unevenness of etch advance inherent in the etching process.

Figure 2:
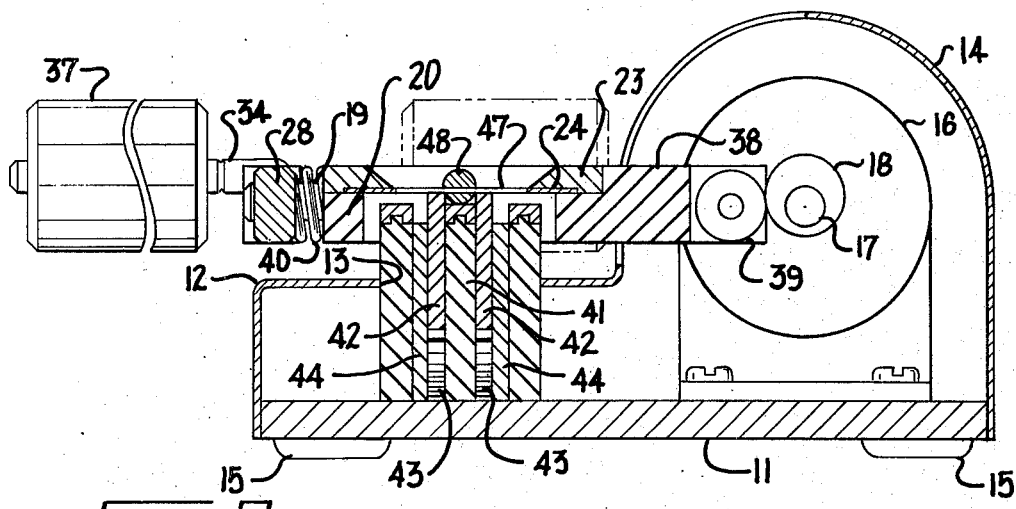
FIG. 2 is a sectional view along the line 2—2 of FIG. 1.

The manner in which the apparatus described above functions will now be discussed. As may be seen in FIGS. 1 and 2 a tube gel 48 may be placed on top of one or more of the gel support pedestals 41 depending upon the width of the tube gel 48. Gel retaining vanes 42 are placed on either side of the gel support pedestal 41 and are held in place by vane retention plates 44. In this fashion, gel 48 is prevented from moving laterally on gel support pedestal 41. Cutting plate holder 20 is lowered to the position where cutting plate 24 and cutting blades 47 overlie tube gel 48. L-shaped rod 32 is oriented with second portion 34 pointing toward pivot axis 27 for low force applied to urge cutting plate holder 20 against tube gel 48, and with second portion 34 extending away from pivot axis 27 for higher forces applied to cutting plate holder 20. Weight 37 is subsequently slid along second portion 34 of L-shaped rod 32 to adjust the force at cutting plate holder 20. It may be seen that the larger the radius from pivot axis 27 of the center of mass of weight 37, the higher the torque generated about pivot axis 27 and the greater the force applied to cutting plate holder 20.

Cutting edge 47A on cutting blades 47 contacts the top edge of gel retention vanes 42 urging them downward against leaf springs 43 due to the force applied thereto by the torque about pivot axis 27 obtained from the radial adjustment of weight 37. Cutting edge 47A does not cut the material from which gel retaining vanes 42 are fabricated. Vanes 42 may be of a telfon (TRADEMARK) material for example.

When motor 16 is actuated, shaft 17 is driven together with cam 18. Cam follower 39, riding on the surface of cam 18 causes cam follower arm 38 to periodically move cutting plate holder 20 against compression springs 40, and consequently cutting blades 47 are moved in a reciprocating motion along the direction of cutting edge 47A which defines a cutting axis. The reciprocating motion of cutting blades 47 causes the serrated cutting edge 47A to slice through tube gel 48 at each of the cutting blades 47 simultaneously. In this fashion an entire tube gel, or strip of slab gel is sliced at once, leaving the individual gel slices free of distortion.

One configuration of cutting plate 24 utilizes a 0.015 inch thick plate with one millimeter spaces between cutting blades 47. The cutting blades, due to the etching action, emerge with a dimension of 0.008 to 0.009 inches at the base and with approximately a 60° angle at cutting edge 47A.

As motor 16 runs and cam 18 imparts the reciprocating motion to cutting blades 47, the blades 47 advance through the gel 48, pushing the gel retaining vanes 42 ahead of the cutting edge 47A and against leaf spring 43. When cutting edge 47A contacts the upper surface of gel support pedestals 41, the gel 48 is completely sliced through simultaneously along its entire length, providing a uniform series of slices without distortion therein. The cutting edge 47A will advance no further upon contacting the surface of gel support pedestal 41.

The method disclosed herein involves holding the gel to be sliced firmly, and forcing a cutting edge against the surface of the gel. The method further involves imparting reciprocating motion to the cutting edge whereby the cutting edges advance through the gel simultaneously thereby cutting the gel into as many slices as there are blades in the cutting plate 24. The reciprocating motion in the direction of the cutting axis has been found to be satisfactory at 0.040 inches amplitude and a frequency of 33 hertz. The trough provided by gel support pedestal 41 and gel retaining vanes 42 has retractable edges as blades 47 force the gel retaining vanes 42 toward the level of the gel support pedestal 41 and against leaf springs 43 due to the force imparted to cutting plate holder 20 by the torque provided by weight 37.

The device disclosed above may be utilized to slice acrylamide gels ranging from 4 to 30 percent concentration. 4 to 5 percent acrylamide gels are generally soft in nature and hard to slice. 7 to 15 percent gels are the easiest to slice. 30 percent concentration gels are "hard" and are therefore the most difficult to slice. A gel slicer for slicing tube gels or strips of slab gels has been disclosed which provides slices of uniform thickness, operates on gels of a wide range of concentrations, avoids distortion in the sliced gels, and simultaneously slices the gel along the entire length thereof.

What is claimed is:

1. Apparatus for slicing an electrophoresed gel comprising means for holding the gel, a plate positioned to overlie said means for holding the gel and having opposing sides and opposing ends, said plate having a plurality of elongate openings therein extending between said opposing sides, a plurality of blade members formed by the portions of said plate between said openings extending between said opposing sides and having a cutting edge thereon on the side facing said means for holding the gel thereby forming substantially parallel cutting axes for said plurality of blade members, means for driving said plate in reciprocating motion along the direction of said cutting axes, and means for urging said plate toward said means for holding, whereby a gel placed in said means for holding is sliced by the reciprocating motion of said plate.

2. Apparatus for slicing an electrophoresed gel comprising a gel support pedestal, first and second retaining vane members positioned on opposite sides of said gel support pedestal, means for resiliently supporting said first and second retaining vane members for urging said vane members to extend beyond the surface of said gel support pedestal, whereby the electrophoresed gel may be placed upon said gel support pedestal for retention thereupon between said vane members, a slicing grid for positioning overlying said gel support pedestal and having opposing sides and opposing ends, a plurality of blade members supported between said opposing sides and having substantially parallel cutting axes extending therebetween, means for driving said slicing grid in reciprocating motion along the direction of said cutting axes, and means for urging said slicing grid toward said gel support pedestal, whereby said plurality of blade members pass through the electrophoresed gel due to the reciprocating motion of said slicing grid and force said first and second vane members to move against said means for resiliently supporting said vane members.

3. Apparatus as in claim 2 together with an additional gel support pedestal for positioning adjacent to said gel support pedestal so that when said first retaining vane is positioned on the opposite side of said additional gel support pedestal, a gel of greater thickness may be retained between said first and second retaining vanes.

4. Apparatus as in claim 1 wherein said means for driving said plate comprises a motor, a rotating shaft driven by said motor, a cam mounted on said rotating shaft, means for mounting said plate, an arm attached to said means for mounting said plate, a cam follower attached to the end of said arm for contacting said cam, said guide means for guiding said means for mounting said plate in the direction of said reciprocating motion.

5. Apparatus as in claim 1 wherein said means for driving said plate comprises a motor, a rotating shaft driven by said motor, a cam mounted on said rotating shaft, means for mounting said plate, an arm attached to said means for mounting said plate, a cam follower attached to the end of said arm for contact with said cam, a framework for mounting said motor, means for rotatably attaching said means for mounting said plate to said framework for positioning about a rotation axis between a position overlying said means for holding and a remote position, and wherein said means for urging comprises an arm extending from and on the same side of said rotation axis as said means for mounting, and a weight slidably attached to said arm for positioning therealong, whereby the force applied to said plate by said means for urging may be adjusted by adjusting the distance of said weight on said arm from said rotation axis.

6. An apparatus for slicing gels comprising a framework, a gel support pedestal for supporting an acrylamide gel, said support pedestal being attached to said framework, first and second planar vane members for positioning on opposite sides of said gel support pedestal, said first and second vane members having a top edge, means for resiliently urging said top edge to a position above said gel support pedestal, a cutting grid movably attached to said framework for alternate positioning overlying said gel support pedestal and remotely therefrom, a plurality of spaced cutting blades in parallel relation on said cutting grid extending in the direction of a cutting axis, means for driving said cutting grid in reciprocating motion along the direction of said cutting axis, and means for forcing said cutting grid toward said gel support pedestal, whereby the gel is retained between said first and second planar vane members and said cutting grid is urged towards said gel support pedestal depressing said means for resiliently supporting said first and second vane members until the gel is simultaneously cut into a plurality of slices.

7. An apparatus comprising a framework, a gel support pedestal, first and second planar vane members for positioning on opposite sides of said gel support pedestal, said first and second vane members having a top edge, means for resiliently urging said top edge to a position above said gel support pedestal, means for holding an acrylamide gel attached to said framework, a cutting grid movably attached to said framework for alternate positioning overlying said means for holding and remotely therefrom, a plurality of spaced cutting blades in parallel relation on said cutting grid extending in the direction of a cutting axis, means for driving said cutting grid in reciprocating motion along the direction of said cutting axis, and means for forcing said cutting grid toward said means for holding an acrylamide gel, whereby a gel may be retained between said first and second planar vane members and said cutting grid is urged towards said gel support pedestal depressing said means for resiliently supporting said first and second vane members until the gel is sliced through to the gel support pedestal by said plurality of spaced cutting blades to form a plurality of gel slices simultaneously.

8. An apparatus as in claim 7 wherein said gel support pedestal comprises a plurality of adjacent pedestals, whereby said first and second planar vane members may be positioned on opposite sides of a predetermined number of said support pedestals for accommodating gels having a predetermined width.

9. An apparatus as in claim 6 wherein said means for driving said cutting grid in reciprocating motion comprises a motor, an output shaft driven rotationally by said motor, a cam mounted on said output shaft, a retaining support for said cutting grid, an arm attached at one end to said retaining support, and a cam follower attached to the other end of said arm for contact with said cam.

10. An apparatus as in claim 9 wherein said means for urging comprises a weight mounted to apply a gravity force to said means for retaining said cutting grid, said weight being adjustable thereby providing a predetermined force to said cutting grid for cutting gels of predetermined concentration.

11. The method of slicing gels comprising the steps of supporting the gel on a pedestal, stopping the gel from lateral movement on the pedestal by contacting the sides thereof with stop members, forcing a plurality of cutting blades against the upper surface of the gel, reciprocating the cutting blade laterally on the gel, and moving the stop members ahead of the cutting blades by the force on the plurality of cutting blades, whereby the cutting blades advance through the gel until they contact the pedestal.

\* \* \* \* \*

UNITED STATES PATENT OFFICE
CERTIFICATE OF CORRECTION

Patent No. 3,994,189　　　　　Dated November 30, 1976

Inventor(s) Stanton A. Hoefer; John C. DiFonzo

It is certified that error appears in the above-identified patent and that said Letters Patent are hereby corrected as shown below:

On the first page of the patent in line 4 of the Abstract after the word "blades", add -- dictate the thickness of the sliced gels and the blades --.

In the drawings, Sheet 1 Figure 1 and Sheet 2 Figure 5, the reference numeral 36 should be applied to the ring element at the end of first portion 33 of rod 32.

Signed and Sealed this

Twenty-fourth Day of May 1977

[SEAL]

Attest:

RUTH C. MASON
*Attesting Officer*

C. MARSHALL DANN
*Commissioner of Patents and Trademarks*